United States Patent [19]

Sezginer

[11] Patent Number: 5,363,041
[45] Date of Patent: Nov. 8, 1994

[54] DETERMINING BOUND AND UNBOUND FLUID VOLUMES USING NUCLEAR MAGNETIC RESONANCE PULSE SEQUENCES

[75] Inventor: Abdurrahman Sezginer, Brookfield, Conn.

[73] Assignee: Schlumberger Technology Corporation, New York, N.Y.

[21] Appl. No.: 999,248

[22] Filed: Dec. 31, 1992

[51] Int. Cl.⁵ .............................................. G01R 33/20
[52] U.S. Cl. .................................... 324/303; 324/300
[58] Field of Search ............... 324/303, 306, 307, 309; 128/653.2, 653.5

[56] References Cited

U.S. PATENT DOCUMENTS

| | | | |
|---|---|---|---|
| 4,728,892 | 3/1988 | Vinegar et al. | 324/303 |
| 4,933,638 | 6/1990 | Kenyon et al. | 324/303 |
| 4,973,111 | 11/1990 | Haacke et al. | 324/309 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |
| 5,218,299 | 6/1993 | Dunkel | 324/307 |

OTHER PUBLICATIONS

"User's Manual," IMSL, Inc., 1987, pp. 309–311.
T. C. Farrar and E. D. Becker, *Pulse and Fourier Transform NMR*, Academic Press, 1971, pp. 18–22.
J. P. Butler et al., "Estimating solutions of first kind integral equations with nonnegative constraints and optimal smoothing," *SIAM J. Numer. Anal.* vol. 18, No. 3, Jun. 1981, pp. 381–397.
L. L. Latour et al., *Journal of Coll. and Interf. Science*, vol. 150, No. 2, May 1992, pp. 535–548.
J. E. Dennis, Jr. and R. B. Schnabel, *Numerical Methods for Unconstrained Optimization and Nonlinear Equations*, Prentice Hall, 1983, pp. 111–152.
M. Abramowitz and I. A. Stegun, Ed., *Handbook of Mathematical Functions*, Dover Publications, 1972, pp. 228–229.
G. H. Golub and C. F. VanLoan, *Matrix Computations*, John Hopkins University Press, 1983, pp. 208–218.
E. Anderson et al., *Lapack Users' Guide*, Society for Industrial and Applied Mathematics, 1992, pp. 25–27.

Primary Examiner—Walter E. Snow
Assistant Examiner—Raymond Y. Mah
Attorney, Agent, or Firm—Leonard W. Pojunas

[57] ABSTRACT

A borehole logging tool comprises a Nuclear Magnetic Resonance (NMR) tool and is pulsed according to a selected sequence. An interpretation is performed which involves a singular value decomposition and compression of data obtained by the tool. The compressed data is then subjected to a nonnegative, linear least square fit to obtain a distribution function. The distribution function is used in determining bound fluid volume, unbound fluid volume, total porosity, spin-lattice relaxation time, spin-spin relaxation time, and mean relaxation time using only the pulse NMR tool.

21 Claims, 6 Drawing Sheets

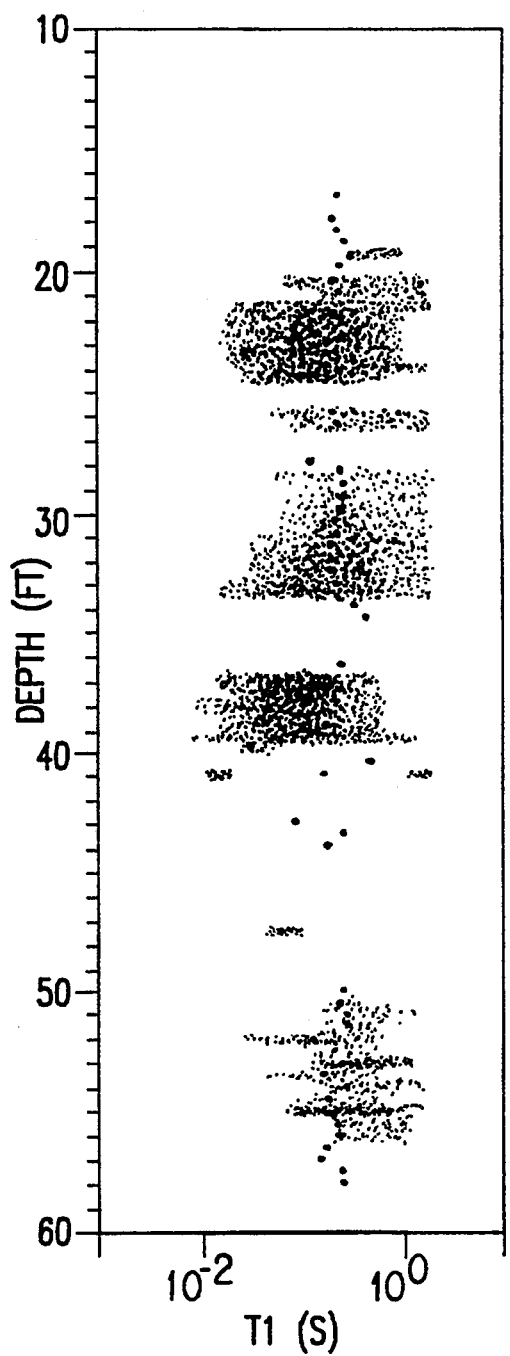
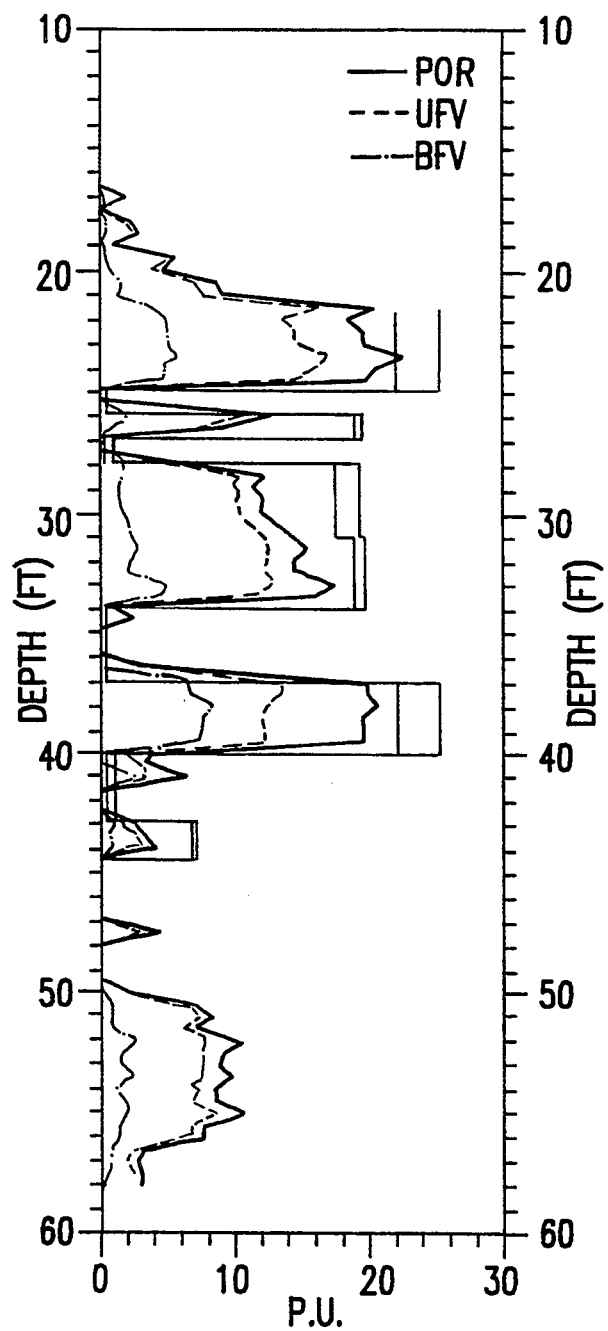
FIG.2C
FIG.2D

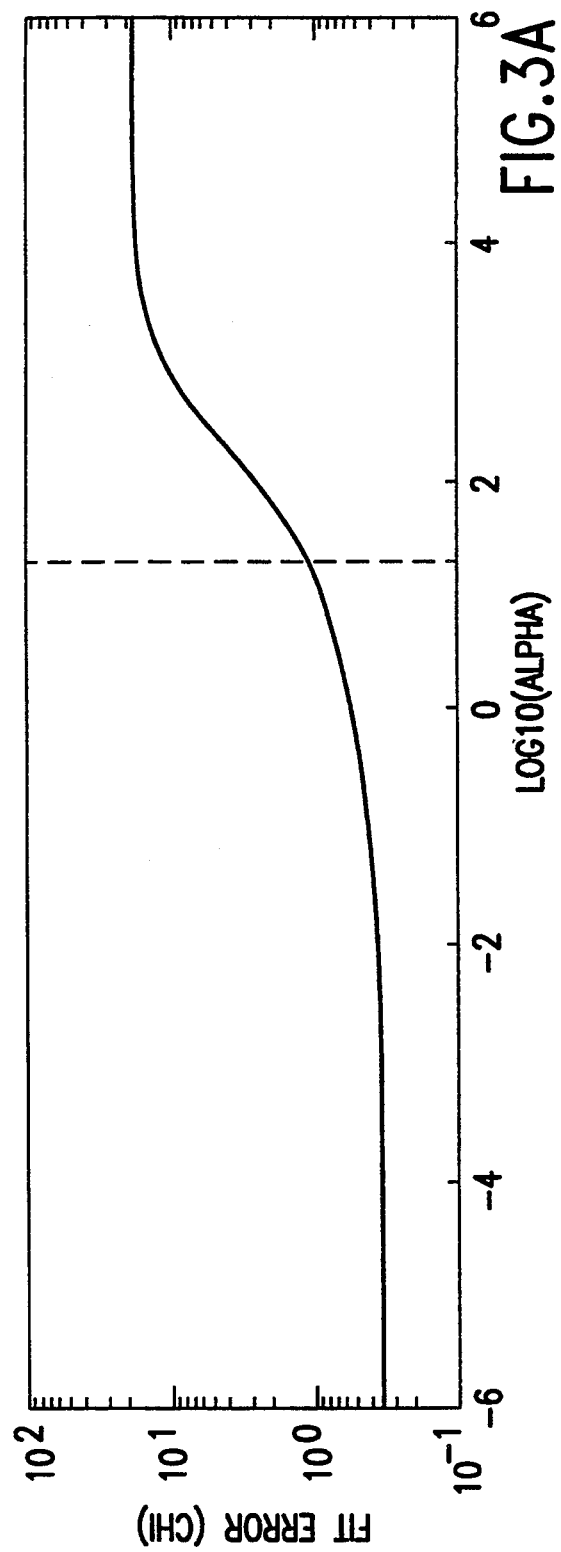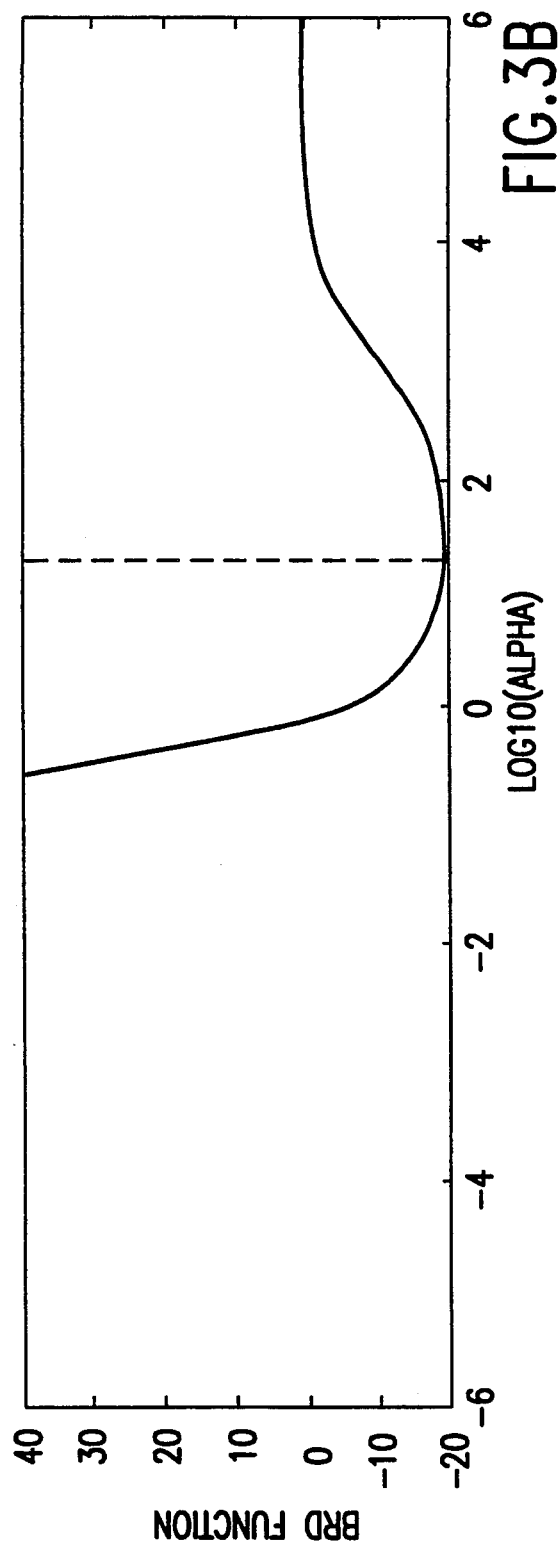

DETERMINING BOUND AND UNBOUND FLUID VOLUMES USING NUCLEAR MAGNETIC RESONANCE PULSE SEQUENCES

FIELD OF THE INVENTION

The invention concerns nuclear magnetic resonance (NMR) pulse sequences which are used in evaluating earth formations. More specifically, the invention relates to NMR pulse sequences which are used by a well logging tool and are interpreted to measure earth formation properties.

BACKGROUND OF THE INVENTION

Cross-reference is made to co-pending U.S. patent application Ser. No. 7/800,339 to A. Sezginer et al. for "Nuclear Magnetic Resonance Pulse Sequences for Detecting Bound Fluid Volume," filed Nov. 27, 1991.

Nuclear magnetic logging tools, such as disclosed in U.S. Pat. Nos. 4,933,638 to Kenyon et al. for "Borehole Measurement of NMR Characteristics of Earth Formations, and Interpretations Thereof"; and 5,055,787 and 5,055,788 both to Kleinberg et al. for "Borehole Measurement of NMR Characteristics of Earth Formations", measure the number and nuclear magnetic resonance (NMR) relaxation rates of hydrogen atoms in the pore space of rocks by measuring the amplitude and decay rate of signals resulting from pulse-echo sequences. In essence, the nuclear magnetic logging tools send a stream of RF-pulses into the formation and monitor the returning pulses which are called spin echoes. The measurements made are typically cyclical, with each cycle taking up to several seconds. Interpretation algorithms are then used to find the formation properties of interest.

The signal measured by a nuclear magnetic logging tool, such as the Pulsed Nuclear Magnetism Tool (PNMT, mark of Schlumberger) is proportional to the mean density of hydrogen nuclei in the fluid that occupies the pore-space. Hydrogen nuclei in the rock matrix relax too rapidly and are not detected by the tool. Since the hydrogen density in water and liquid hydrocarbons are approximately constant, the detected signal can be calibrated to give the volume fraction of the fluid occupying the pore space.

NMR relaxation of a water saturated porous rock is not a simple exponential relaxation, but it is a continuous superposition of exponential relaxations. For example, in an inversion-recovery (Farrar, T. C. and E. D. Becker, *Pulse and Fourier Transform NMR*, Academic Press, 1971) experiment, the signal obtained after an inversion and a recovery time of length t is $$m(t) = \int_0^\infty a(T_1)(1 - 2e^{-t/T_1})dT_1$$

Loosely speaking, $a(T_1)dT_1$ is the volume fraction of the fluid whose relaxation time is between $T_1$ and $T_1+dT_1$, where $T_1$ is spin-lattice relaxation time. This interpretation is approximately correct because pores of rocks are in a fast diffusion regime (Latour, L. L., R. L. Kleinberg and A. Sezginer, Journal of Coil. and Interf. Science, Vol. 150, No. 2, May 1992) where the NMR signal from each pore is approximately single-exponential, and the relaxation time is proportional to the volume to surface ratio of the pore. Several researchers have demonstrated for water saturated sandstones that the pore size distribution is closely related to the distribution of NMR relaxation times.

Short relaxations times are due to water that is bound to clay minerals or water in pores that are too small to be flushed by a feasible pressure gradient. Also, heavy (viscous) hydrocarbons have shorter relaxation times. Fluids that relax slowly have low viscosity and reside in large pores. Hence, the slowly relaxing fluids can be produced, that is, pumped to the surface, provided there is sufficient permeability. It is therefore important to quantify the volume of the slowly relaxing fluids.

U.S. patent application Ser. No. 7/800,339 describes an NMR pulse sequence for use in a Pulsed Nuclear Magnetic borehole logging tool (PNMT). The pulse sequence includes a series of CPMG pulses according to:

$$T_r - 90°\pm x - (t_{cp} - 180°_y - t_{cp} - echo_j)$$

where j is the index of CPMG echoes gathered. $T_r$ is the wait time, $t_{cp}$ is the Carr-Purcell spacing. This pulse sequence is used to determine Bound Fluid Volume (BFV) which is subtracted from total porosity to yield Unbound Fluid Volume (UFV) of a formation surrounding the borehole. Measuring the BVF, the amount of rapidly relaxing fluid (that fluid having a spin-spin relaxation time which is less than 33 ms), is more efficient than measuring UFV (up to 2 secs), and is insensitive to motion of the logging tool. However, with this technique, another logging tool is required to determine total porosity. Alternatively, the PNMT itself can be used to determine porosity, however, this is a relatively time consuming technique, which would require two logging passes.

OBJECTS AND SUMMARY OF THE INVENTION

It is an object of the invention to provide an NMR pulse sequence logging tool, which, when used alone in a continuous logging mode, indicates bound fluid volume, unbound fluid volume, total porosity, distribution of spin-spin relaxation times, and mean relaxation time of an earth formation.

The inventors have found a technique for estimating the distribution of relaxation times; porosity; bound and unbound fluid volumes and mean relaxation time. The technique results in the direct output of these values as a function of depth using a PNMT. This novel technique is applicable to continuously moving and stationary modes of logging a borehole with the PNMT.

This invention concerns a method for evaluating an earth formation with a borehole tool. The tool includes a means for producing static magnetic fields in a volume of a formation, means for producing oscillating magnetic fields in a volume of a formation, and means for measuring an induced magnetic signal. Steps of the method include:

a) producing a static magnetic field in the volume of formation;

b) producing oscillating magnetic fields according to a pulse sequence $$T_r - 90°\pm x - (t_{cp} - 180°_y - t_{cp} - echo_j)$$

where j=1, 2 . . . . N, and N is the number of 180° RF-pulses in a single Carr-Purcell-Meiboom-Gill (CPMG) sequence in order to induce signals in the volume which are measurable by the tool in the borehole;
where $T_r$ is recovery time before a CPMG sequence, and
where $t_{cp}$ is the Carr-Purcell spacing;
c) using a linear operator to map a relaxation-time distribution to resulting spin echoes;
d) producing a singular value decompositon (SVD) of the linear operator according to the pulse sequence;
e) measuring with the tool the induced signals; and
f) determining from the measured signals an indication of unbound fluid volume of the volume of earth formation in light of the SVD output.

BRIEF DESCRIPTION OF THE FIGURES

FIGS. 2A–2D are charts illustrating logs of a formation and revealing porosity, BFV, and UFV according to the invention.

FIGS. 3A and 3B respectively illustrate a normalized fit error and a Butler-Reeds-Dawson function.

DETAILED DESCRIPTION OF THE INVENTION

Measuring formation properties, such as spin-lattice relaxation time (T1); spin-spin relaxation time (T2) and total porosity ($\theta$) using NMR logging tools are described in U.S. Pat. No. 5,023,551 to Kleinberg et al. for "Nuclear Magnetic Resonance Pulse Sequences for Use with Borehole Logging Tools". The specification of U.S. Pat. No. 5,023,551 is incorporated by reference and is assigned to the same assignee as this invention.

Producible fluids in porous rocks are distinguished by their slow Nuclear Magnetic Resonance (NMR) relaxation times. However, to measure the producible fluid (the unbound fluid volume (UFV)) requires an immense amount of data gathering of relaxation times, many of which can reach the order of 2 seconds, using numerous iterations of the pulse sequence described in U.S. Pat. No. 5,023,551 and a subsequent interpretation of that great amount of data. Such a technique is relatively time consuming and prohibits logging at speeds that are standard in the business (1800–3600 ft/hr). Rapidly relaxing fluids (T1 less than 50 ms, for example) are bound to the rock, so they are not producible. As described in U.S. patent application Ser. No. 7/800,339, to Sezginer for Nuclear Magnetic Resonance Pulse Sequences for Determining Bound Fluid Volume, and summarized in the section below entitled "DETERMINATION OF BOUND FLUID VOLUME" NMR can be used to estimate the unbound fluid volume (UFV) if porosity is determined using another logging tool (such as the LDT or CNL, both marks of Schlumberger Technology Corporation, discussed below). Specifically, using NMR well logging techniques, bound fluid volume (BFV) is measured, and subtracted from total porosity $\phi$ obtained from another tool to estimate unbound fluid volume (UFV). The estimation of UFV indicates the amount of producible fluid in a formation being logged.

Figure 1:
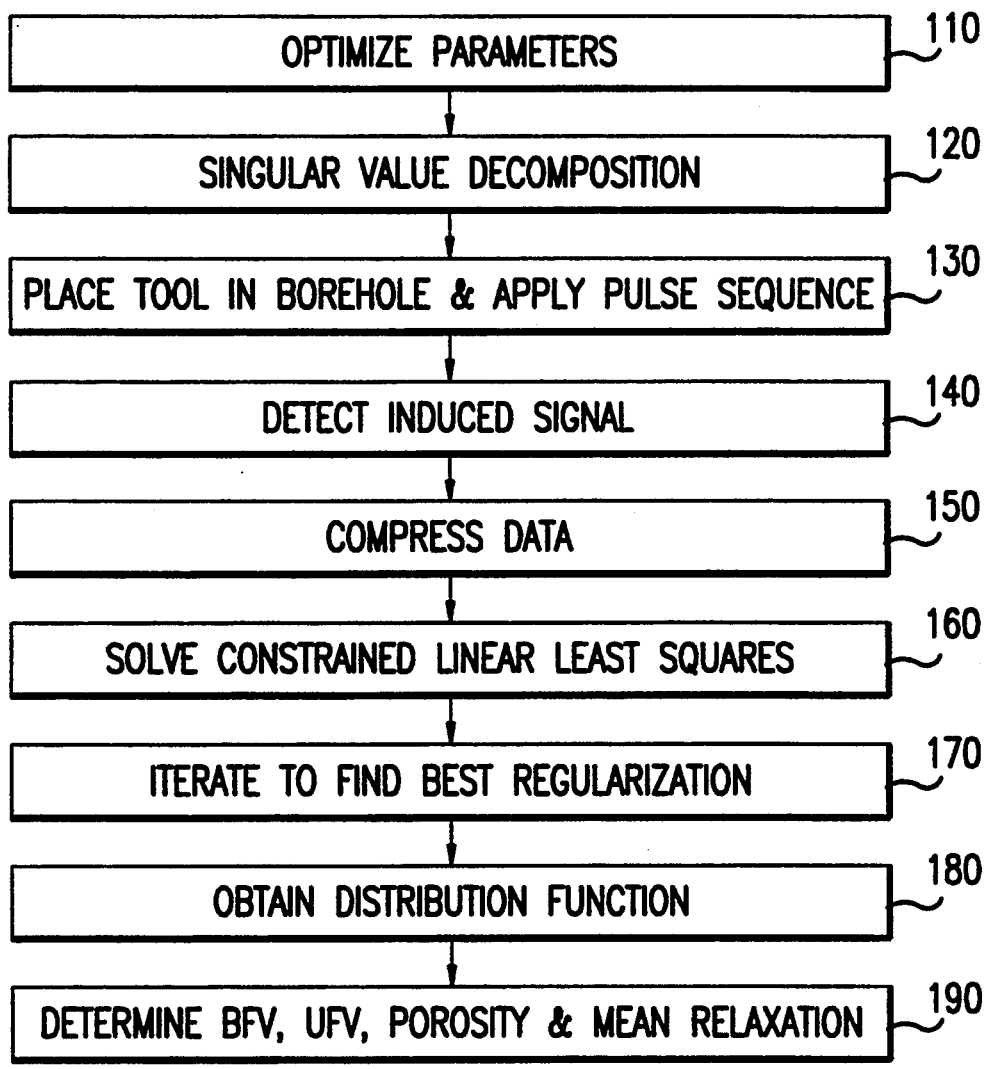
FIG. 1 is a flow chart illustrating steps for determining mean relaxation, porosity, Bound Fluid Volume (BFV), and Unbound Fluid Volume (UFV) of a formation.

FIG. 1 is a flow chart illustrating steps for determining mean relaxation, porosity, Bound Fluid Volume (BFV) and Unbound Fluid Volume (UFV) of a formation. UFV is the amount of producible fluid that is contained in the formation around the borehole being logged. These steps are discussed in detail below. At 110, optimal parameters and tool constants are determined as described in the section "DETERMINATION OF BOUND FLUID VOLUME" below and U.S. Pat. No. 5,023,551 to Kleinberg et al. At 120, a singular value decomposition is performed. Typically, singular value decomposition 120 is performed before logging actually begins and the values are stored in memory within the PNMT or the surface computer. The singular value decomposition 120, depends on the number of echoes, recovery time, echo spacing, and on the interval $[T_a, T_b]$ which is assumed to be the support of the relaxation-time distribution. Also, a constant T1/T2 is assumed and a range for T2 is assumed. The singular value decomposition of the operator that maps the relaxation time distribution to the spin echoes is determined as detailed in the section "DETECTION OF THE SINGULAR VALUE DECOMPOSITION, STEP 120" below. This operation yields the singular values $s_j$, the left singular vectors $u_j$, and the right singular functions $v_j$ for $j=1,2 \ldots r$. At 130, a PNMT logging tool, for example, is placed in the borehole and a pulse sequence is applied as described in U.S. Pat. No. 5,023,551 to Kleinberg et al. Specifically, the PNMT produces a static magnetic field in the volume of formation and then produces oscillating magnetic fields according to a pulse sequence $$T_r - 90°_{\pm x} - (t_{cp} - 180°_y - t_{cp} - \text{echo}_j)$$

where $j=1,2, \ldots N$, and N is the number of echoes collected in a single Carr-Purcell-Meiboom-Gill (CPMG) sequence to induce signals in the volume which are measurable by the PNMT in the borehole; where $T_r$ is recovery time before a CPMG sequence, and where $t_{cp}$ is the Carr-Purcell spacing. This pulse sequence is also discussed below. At 140, the PNMT then detects resulting signals which have been induced in the formation around the borehole as described in U.S. Pat. No. 5,023,551. For each CPMG sequence the recovery time (Tr) is the same. At 150, the raw field dam is compressed by the operation $\bar{y} = [u_1; u_2; \ldots u_r]^T Y$. According to this technique, the data can be compressed without discarding information. At 160, a constrained regularized nonnegative least squares is performed in order to fit the compressed data of 150. The purpose is to estimate a distribution of spin-spin relaxation times, which is similar to a probability density function, from the compressed data.

At 170, an iteration is performed to find a best regularization parameter using the singular value decomposition of 120. This yields, at 180 the relaxation-time distribution function. At 190, Unbound Fluid Volume UFV, Bound Fluid Volume BFV, porosity and mean relaxation times are determined from the distribution function after nested minimizations are completed.

PREFERRED MEASUREMENT PROTOCOL

The preferred pulsed-NMR measurement protocol for the mode of logging in which the sonde is continuously moving is as follows: after a $T_r$-second recovery time, a Carr-Purcell pulse-echo sequence with Meiboom-Gill's modification (CPMG) is performed. During each CPMG sequence, N spin-echoes that are separated by $2t_{cp}$ seconds are recorded.

$$\text{CPMG}^{(\pm)} = 90°_{\pm x} (t_{cp} \, 180°_y \, t_{cp} \pm \text{echo}_j)_{j=1,2,3 \ldots N} \quad (1)$$

The phase of the $90°_x$ RF-pulse at the beginning of the CPMG sequences is alternated by 180° in order to cancel baseline errors. The overall measurement protocol is as follows:

$$T_r \text{CPMG}^{(+)} \, T_r \, \text{CPMG}^{(-)} \, T_r \, \text{CPMG}^{(+)} \, T_r \, \text{CPMG}^{(-)} \quad (2)$$

where $T_r$ indicates the recovery period, typically 0.5–2.0 seconds. Typical values of the echo-spacing, recovery-time, and number of echoes per CPMG are 2 $t_{cp}$=100–500 μts, and N=300–1000.

MODEL OF THE SIGNAL AND NOISE

The input to the processing algorithm is a vector y that contains the echoes in a CPMG. The vector y is obtained by combining one or more pairs of phase alternated CPMG sequences. In this manner, pairs of CPMG sequences are combined. The measured vector y consists of signal and additive noise (thermal noise generated in the RF antenna accounts for most of the noise. There is also some noise generated in the receiver electronics.):

$$y = \epsilon + f \quad (3)$$

$$\epsilon = N(0, \sigma^2 I_{N \times N}) \quad (4)$$

$$f = \begin{pmatrix} \langle g_1, f \rangle \\ \langle g_2, f \rangle \\ \vdots \\ \langle g_N, f \rangle \end{pmatrix} \quad (5)$$

$$\langle g_j, f \rangle = \int_{\log T_a}^{\log T_b} g_j f(\log T_2) d(\log T_2) \quad (6)$$

$$g_j = (1 - e^{-T_r/T_2}) e^{-2jt_{cp}/T_2} \quad (7)$$

$$\xi = T_1/T_2 \quad (8)$$

$g_j$ is the measurement kernel. It would be proportional to the magnitude of the jth spin-echo, if the sample had a well-defined single exponential relaxation rate.

(g, f) = inner product of the functions g and f $$\langle g, f \rangle = \int_{\log T_a}^{\log T_b} g(T_2) f(T_2) d(\log T_2)$$

y = vector of N measurements (spin-echoes) and (4) means $\epsilon$ is a Normal (Gaussian) random vector of 0 mean. Its covariance is $\sigma^2 I_{N \times N}$, where $I_{N \times N}$ is the N by N identity matrix. The entries of the vector $\epsilon$ are identically and independently distributed Gaussian variables of zero mean and the standard deviation of each one is $\sigma$.

The determination of $\sigma^2$ is described in the section "STACKING DATA, DETERMINING $\sigma^2$ AND THE PHASE" below. The measured value of each spin-echo is a linear projection of the distribution function f. The distribution function indicates the density of pore-volume with respect to the logarithm of the relaxation time. In other words, $f(\log T_2) dT_2/T_2$ is the fractional volume (in porosity units) of the fluids whose relaxation time is between $T_2$ and $T_2+dT_2$. Distributions with respect to $T_2$ or $1/T_2$ can be obtained by multiplying $f(\log T_2)$ by $1/T_2$ or $T_2$, respectively. The distribution with respect to the variable $\log T_2$ is preferred because the NMR relaxation-times of rocks span three decades. The relaxation times are assumed to be distributed between $T_a$ and $T_b$. These limits should be selected such that $T_a > 2t_{cp}$ and $T_b < T_r$. $T_a$ and $T_b$ define the range of observable relaxation rates. The observable relaxation time of any pore is assumed to be between $T_a$ and $T_b$. ($T_a$ is about 1 ms and $T_b$ is about 1 s).

Unbound and bound fluid volumes and porosity are related to the distribution function as follows:

$$UFV = \int_{\log T_a}^{\log T_c} f(\log T_2) d\log T_2 \quad (9)$$

$$BFV = \int_{\log T_c}^{\log T_b} f(\log T_2) d\log T_2 \quad (10)$$

$$\Phi = UFV + BFV \quad (11)$$

where $\Phi$ is porosity, the total volume fraction of fluids in the rock. The cutoff relaxation time $T_c$ distinguishing BFV from UFV is empirically determined to be 33 ms for water saturated sandstones. The projection kernels $g_j$ are viewed as functions of $T_2$ and $\xi = T_1/T_2$ is assumed constant ($\xi$=1.5).

DATA COMPRESSION. STEP 150

The operator $K:L_2[\log T_a, \log T] \to R^N$ is a compact linear operator of finite rank (no greater than N). Its kernels $g_j$ are linearly independent but only marginally. The entries of the data vector y are almost redundant. Therefore, the data can be significantly compressed according to step 180 of FIG. 1 without discarding information. For this purpose, consider the singular value decomposition of the operator K:

$$f = \sum_{j=1}^{N} u_j s_j \langle v_j, f \rangle \quad (12)$$

where $s_j$ is a singular value greater than zero, $u_j$ are orthonormal vectors and $v_j$ are orthonormal functions:

$$u_i^T u_j = \delta_{ij}; \; u_j \in R^N, \; i, j=1, 2, \ldots, N \quad (13)$$

$$(v_i, v_j) = \delta_{ij}; \; v_j \in L_2[\log T_a, \log T_b], \; i, j=1,2 \ldots, N \quad (14)$$

$$s_1 \geq s_2 \geq \ldots \geq s_N > 0 \quad (15)$$

The linear operator K is a function of the number of echoes, recovery time, echo spacing, an assumed constant value for $T_1/T_2$, and an assumed range for $T_2$ (for the domain of f).

The singular values $s_j$ rapidly approach zero as j increases. Therefore, the operator can be split into a significant pan $K_r$ and a remainder:

$$y = K_r f + (K - K_r) f + \epsilon \quad (16)$$

$$K_r f = \sum_{j=1}^{r} u_j s_j \langle v_j, f \rangle \quad (17)$$

-continued $$\|K - K_r\| = s_{r+1} \quad (18)$$

If the index r is chosen such that $$s_{r+1}f < E[\epsilon^2]^{\frac{1}{2}} = \sqrt{N}\,\sigma \quad (19)$$

then the second part of the operator is negligible:

$$y \approx K_r f + \epsilon \quad (20)$$

Since $\{u_1, u_2, \ldots, u_N\}$ is a basis for $R^N$, (20) is equivalent to $$\tilde{y} \approx \tilde{\epsilon} + \begin{pmatrix} \langle s_1 v_1, f \rangle \\ \langle s_2 v_2, f \rangle \\ \langle s_r v_r, f \rangle \end{pmatrix} \quad (21)$$

$$\tilde{y} = [u_1 u_2 \ldots \mu_r]^T y \quad (22)$$

$$\tilde{\epsilon} = [u_1 u_2 \ldots \mu_r]^T \epsilon \quad (23)$$

$$\tilde{\epsilon} = N(0, \sigma^2 I_{rxr}) \quad (24)$$

Under typical conditions, $r=5$ is ample for representing borehole NMR data. Thus the dimension of the compressed data vector y is only 5, yet it contains almost all the information the 500–1000 dimensional data vector y contains. This approach to a general linear inverse problem per se is well known. Data compression significantly speeds up the computation explained in the next section.

REGULARIZED NONNEGATIVE LEAST SQUARES FIT TO THE COMPRESSED DATA, STEP 160

The purpose of this section is to obtain an estimate of the distribution f from the compressed data $\bar{y}$ by solving the constrained linear least squares problem to obtain such a distribution. See step 160 of FIG. 1. Since f is the a distribution (similar to a probability density function), it must be nonnegative. The algorithm summarized below is discussed in detail by Butler, J. P., J. A. Reeds, and S. V. Dawson, "Estimating Solutions of First Kind Integral Equations with Nonnegative Constraints and Optimal Smoothing," SIAM J. Numer. Anal., Vol. 18, No. 3, 381–397, 1981. The function f is found by minimizing a regularized error functional:

$$f_\alpha = \underset{f \geq 0}{\operatorname{argmin}} \left\{ \sum_{j=1}^{r} (\langle s_j v_j, f \rangle - y_j)^2 + \alpha \langle f, f \rangle \right\} \quad (25)$$

There is always a unique solution to (25) and the solution is necessarily of the following form:

$$f_\alpha = \left( \sum_{j=1}^{r} c_j s_j v_j \right) H \left( \sum_{j=1}^{r} c_j s_j v_j \right) \quad (26)$$

where H is the Heaviside step function and the coefficient vector $c(\alpha) = [c_1\, c_2 \ldots c_N]^T$ satisfies the following equation:

$$[\alpha I + M(c)]c(\alpha) = \bar{y} \quad (26.1)$$

where M(c) is an $N \times N$ symmetric and positive-semidefinite matrix defined below. Matrix M depends on the coefficient vector c. Therefore, solution of (26.1) for c is necessarily iterative. The vector $c(\alpha)$ that satisfies (26.1) is also the unique vector minimizing the following expression:

$$c_\alpha = \operatorname{argmin} \Psi(c, \bar{y}, \alpha) \quad (27)$$

$$\Psi(c, \bar{y}, \alpha) = \frac{1}{2} c^T(M(c) + \alpha I)c - c^T \bar{y} \quad (28)$$

$$M_{ij}(c) = s_i s_j \int_{\log T_a}^{\log T_b} v_i v_j H\left( \sum_{j=1}^{r} c_j s_j v_j \right) d\log T_1 \quad (29)$$

There are no constraints on the vector $c=[c_1, c_2, \ldots c_r]^T$. The derivatives of $\psi$ with respect to c have the following exact expressions:

$$\nabla_c \psi = (M(c) + \alpha I)c - \bar{y} \quad (30)$$

$$\nabla_c \nabla_c^T \psi = M(c) + \alpha I \quad (31)$$

The hessian matrix $\nabla_c \nabla_c^T \psi$ is positive definite. $\psi$ is minimized with respect to c using the modified-Newton's algorithm with line-search. The minimization is as follows:

MINIMIZATION OF $\psi$

STEP 1: Evaluate M(c), $\psi$, $\nabla_c \psi$ and $\nabla_c \nabla_c^T \psi$ for the current value of c.

STEP 2: Evaluate the Newton-step:

$$= -(\nabla_c \nabla_c^T)^{-1} \nabla_c \psi \quad (32)$$

STEP 3: Line-search: find $\mu > 0$ such that $$f_\alpha = \left( \sum_{j=1}^{r} c_j s_j v_j \right) H(\psi(c + \mu p, \bar{y}, \alpha) < \psi(c, \bar{y}, \alpha) + \quad (33)$$

$$\eta \mu p^T \nabla_c \psi(c, \bar{y}, \alpha)\ \text{and})$$

$$p^T \nabla_c \psi(c + \mu p, \bar{y}, \alpha) > \beta p^T \nabla_c \psi(c, \bar{y}, \alpha) \quad (34)$$

where $\eta = 0.0001$ and $\beta = 0.99$ are constants. The final result of the iteration does not depend on $\eta$ and $\beta$.

STEP 4: Update $c \rightarrow c + \mu p$ and go to STEP 1.

Minimization per se has been described by Dennis, J. E., Jr. and R. B. Schnabel, *Numerical Methods for Unconstrained Optimization and Nonlinear Equations*, Prentice Hall, Inc., Englewood Cliffs, N.J., 1983.

SELECTION OF THE OPTIMAL REGULARIZATION PARAMETER, STEP 170

There is an optimal value or range of values for the regularization parameter cc because if $\alpha$ is too small, the problem is ill-conditioned and the end result is too sensitive to random measurement noise. On the othe hand, if it is too large, a systematic error is introduced because $f_\alpha$ that minimizes (25) no longer fits observations. In the extreme limit, $\lim_{\alpha \to \infty} f_\alpha = 0$ irrespective of the data. Ideally, the optimal regularization parameter $\alpha_0$ is the one that minimizes $\|f_\alpha - f\|$ However, this operation cannot be carried out since the actual distribution f is unknown. There are several ad hoc algorithms to find a suitable regularization parameter. All of these algorithms have a goal that can be rigorously stated but derived only by qualitative arguments. These algorithms have two nested nonlinear minimizations: the inner iteration calculates $f_\alpha$ using Algorithm (42) and the outer iteration searches a suitable value of $\alpha$ (see FIG. 1).

Dependence of the Fit Error on $\alpha$

The operator K maps the solution $f_\alpha$ to $$Kf_\alpha = Mc \tag{35}$$

According to (26.1) and (35) the residual vector is equal to $$\tilde{y} - Kf_\alpha = \alpha c(\alpha) \tag{36}$$

We define the fit error $\chi(\alpha)$ as the length of the residual vector:

$$\chi(\alpha) = \|\tilde{y} - Kf_\alpha\| \tag{37}$$

$$= \alpha \|c\| \tag{38}$$

Once the vector c is computed, the fit error is readily evaluated by (38) without forming the residual $\|Kf_\alpha - \tilde{y}\|$. The derivative of the fit error with respect to the regularization parameter is also readily computed:

$$\frac{d\chi}{d\alpha} = \|c\| + \frac{\alpha}{\|c\|} c^T \frac{dc}{d\alpha} \tag{39}$$

$$= \|c\| - \frac{\alpha}{\|c\|} c^T (\alpha I + M)^{-1} c \tag{40}$$

The last equation is obtained by $$\frac{dc}{d\alpha} = -(\alpha I + M)^{-1} c \tag{41}$$

which is in turn obtained by differentiating (26.1) with respect to $\alpha$ and using the property $$\frac{dM}{d\alpha} c = 0 \tag{42}$$

The slope of the log-log plot of the function $\chi(\alpha)$ is:

$$\frac{d(\log\chi)}{d(\log\alpha)} = 1 - \left(\frac{c}{\|c\|}\right)^T (I + M/\alpha)^{-1} \left(\frac{c}{\|c\|}\right) \tag{43}$$

Since M is a positive-semidefinite matrix, it follows from (43) that $$0 \leq \frac{d(\log\chi)}{d(\log\alpha)} \leq 1 \tag{44}$$

The fit error is a monotone increasing function of the regularization parameter for $\alpha > 0$. The log-log plot of $\chi(\alpha)$ becomes flat for large $\alpha$:

$$\lim_{\alpha \to \infty} \frac{d(\log\chi)}{d(\log\alpha)} = 0 \tag{45}$$

$$\lim_{\alpha \to \infty} \chi(\alpha) = \|\tilde{y}\| \tag{46}$$

For small $\alpha$, $$\lim_{\alpha \to \infty} \frac{d(\log\chi)}{d(\log\alpha)} = \begin{cases} 1, & \text{if } \inf_{f \geq 0} |Kf - \tilde{y}| = 0 \\ 0, & \text{if } \inf_{f \geq 0} |Kf - \tilde{y}| > 0 \end{cases} \tag{47}$$

S-Curve Method

When $$\inf_{f \geq 0} \|Kf - \tilde{y}\| > 0$$

the log-log plot of $\chi(\alpha)$ assumes an S-shape as shown in the graph in FIG. 3A. In that case, as $\alpha$ is decreased beyond the heel of the s-curve of $\chi(\alpha)$, the fit error does not significantly decrease, but the distribution $f\alpha$ becomes more oscillatory and larger in the 2-norm. Therefore, the values of $\alpha$ around the heel of the s-curve in the log-log plot of $\chi(\alpha)$ are optimal in the sense that they give largest amount of detail in $f_\alpha$ that can be justified by the data. In the s-curve method, the regularization parameter is chosen as the smallest value of $\alpha$ that satisfies $$\frac{d(\log\chi)}{d(\log\alpha)} = tol \tag{48}$$

where $0 < tol < 1$ is a prefixed constant close to zero. In this work, tol $= 0.1$ was used. The regularization parameter defined by (48), hence $f_\alpha$, depends on the constant tol. Smaller tol will yield smaller $\alpha$. At this point, the reader may rightfully question the wisdom of replacing one undetermined parameter ($\alpha$) with another (tol) at considerable computational cost. The parameter tol has the advantage of being data independent: it can be set to a constant irrespective of the measurement noise level.

Equation (48) is solved numerically using (40) to compute $d\chi/d\alpha$. Unfortunately, there is not a similar analytic expression for the second derivative of $\chi$.

The s-curve method is not applicable when $$\inf_{f \geq 0} \|Kf - \tilde{y}\| = 0$$

In that case the following approach works.

Butler-Reeds-Dawson (BRD) Method

Butler, Reeds and Dawson [1981] start with the following rigorous statement:

$$\underset{\alpha}{\operatorname{argmin}} \|f_\alpha - f\| = \underset{\alpha}{\operatorname{argmin}} \|f_\alpha - f\| - \|f\| \tag{49}$$

$$= \operatorname*{argmin}_{\alpha} c^T Mc - 2 \sum_{i=1}^{N} c_i <k_i(x)H(f_\alpha(x)), f> \qquad (50)$$

Then, BRD hypothesize that the support of f(x), the actual distribution, is contained in the support of $f_\alpha(x)$, which is the estimate of the distribution. This hypothesis is very plausible since $f_\alpha$ is a smoothed version off when $\alpha > 0$; nevertheless, it is an unproven statement. At this point they obtain $$\operatorname*{argmin}_{\alpha} \|f_\alpha - f\| \approx \operatorname*{argmin}_{\alpha} c^T Mc - 2c^T \tilde{y} + 2c^T(\text{noise}) \qquad (51)$$

The exact value of the noise vector is as unknown as the solution f. To proceed further, BRD replace the only unknown term in (51), namely $c^T$(noise), by $$\|c\| \sqrt{r\sigma}$$

which is a conservatively large estimate of its random magnitude.

$$\operatorname*{argmin}_{\alpha} \|f_\alpha - f\| \approx \operatorname*{argmin}_{\alpha} h(\alpha)$$

$$h(\alpha) = c^T Mc - 2c^T \tilde{y} + 2\|c\| \sqrt{r\sigma}$$

The minimization of the BRD function $h(\alpha)$ is simplified by the availability of an analytic expression for its derivative; there is not a similar simple expression for its second derivative:

$$\frac{dh(\alpha)}{d\alpha} = \left(\alpha - \frac{\sigma \sqrt{r}}{\|c\|}\right) c^T(\alpha I + M)^{-1} c \qquad (52)$$

BRD prove that $h(\alpha)$ has a unique minimum at $$\alpha_{opt} = \sigma \sqrt{r} / \|c\| \quad \text{provided that}$$

$$\inf_{f \geq 0} \|Kf - \tilde{y}\|^2 < r\sigma^2 < \|\tilde{y}\| \qquad (53)$$

Otherwise, if the data quality is poor ($r\sigma^2 \geq \|d\|$), then $\alpha_{topt} = \infty$ and $f_\alpha = 0$. More disconcerting yet, BRD algorithm fails (yields $\alpha = 0$) when $$\inf_{f \geq 0} \|Kf - \tilde{y}\|^2 \geq r\sigma^2 < \|\tilde{y}\| \qquad (54)$$

The probability of this event is by no means negligible; it occasionally occurs when processing compressed PNMT data. In that case, $\alpha$ is determined by (48) using the s-curve method.

BRD algorithm requires a priori knowledge of the data variance $\sigma^2$, which is easily obtained from the PNMT data.

Preferred Regularization Search

In this work, the maximum of the $\alpha$ parameters determined by the BRD method and the S-Curve method is used as the regularization parameter. This is a robust scheme because according to (47) and (54), these two algorithms cannot simultaneously fail to give a positive $\alpha$. The two regularization algorithms are not run separately: there is ony one iteration loop for $\alpha$ with two stopping conditions.

AN EXAMPLE

Figure 2A:
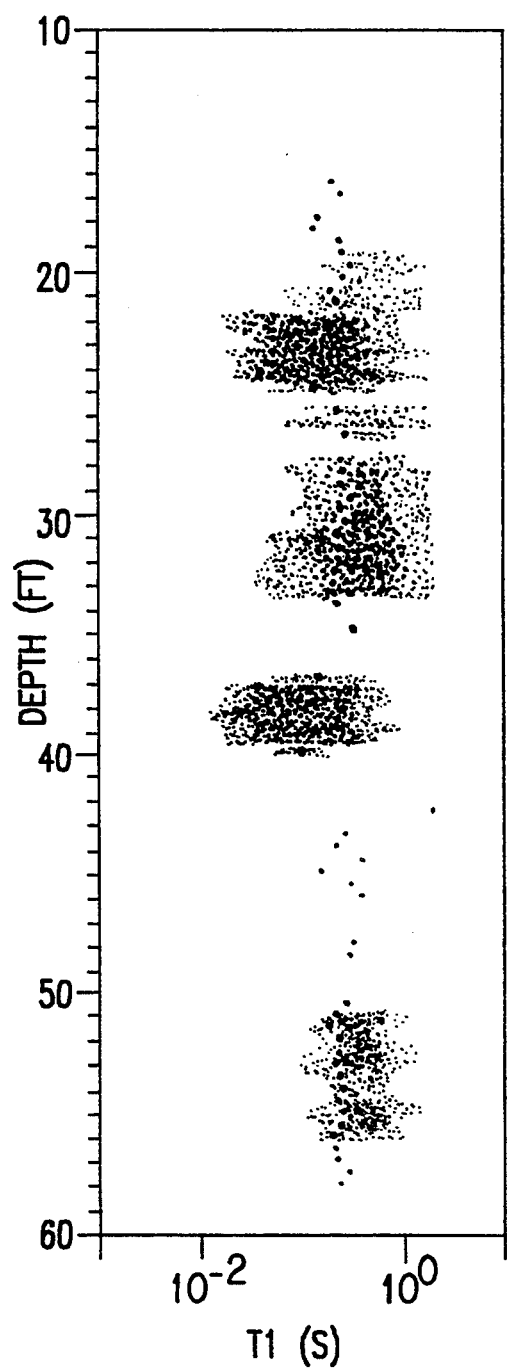
Figure 2B:
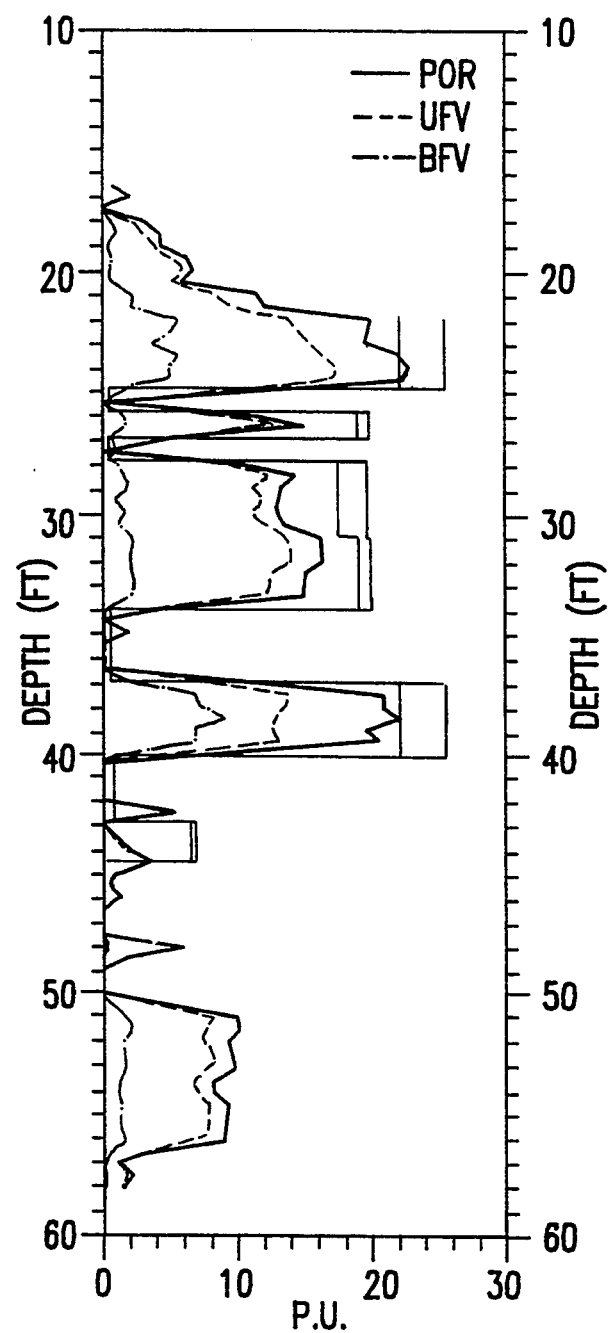

An example is shown in FIGS. 2A–D. The data was collected in a continuous logging mode using the PNMT at the CAT-C test well at Schlumberger Well Services at Houston on Oct. 30, 1991. The test well had been drilled in an artificial formation made of a sequence of quarried rocks. FIGS. 2A, 2B show a log run at one speed and FIGS. 2C, 2D show a log run at another speed.

On the fight track FIGS. 2B, 2D, the porosity (the continuous curve), the unbound fluid volume (the dashed curve), and their difference, the bound fluid volume (the chain-dashed curve) are shown. The dotted blocked lines indicate the upper and lower porosity values measured by a buoyancy method in the laboratory. These measurements were performed on 3–4 plugs taken from each type of rock in the artificial formation.

The relaxation-time distribution function is displayed on the left track, FIGS. 2A, 2C as a grey-scale plot. Darker shades indicate larger density of fluid volume with respect to the relaxation time. The dots indicate the logarithmic mean of the distribution. The agreement between the FIGS. 2A and 2B, and between FIGS. 2C and 2D is apparent.

OTHER MEASUREMENT PROTOCOLS

The technique presented here is not limited to the preferred measurement protocol (2). It can also be used with the conventional inversion-recovery measurement or the FIR/CPMG measurement, which is the preferred protocol for stationary measurements. When used in the continuous logging mode, the FIR/CPMG protocol may have a problem with bed boundaries. Specifically, data points on the spin-lattice relaxation curve are sometimes obtained from disjoint sections of the formation, which yields erratic estimates of the relaxation-time around the bed boundaries. The processing of the FIR/CPMG data was discussed in U.S. Pat. No. 5,023,441. The protocol (2) solves this problem because all of its CPMG sequences are functionally similar, that is, any one of them has all the data that is needed for the inversion. With the technique of this invention, there is little chance that neighboring points on the decay curve belong to disjoint sections of the formation.

STACKING DATA, DETERMINING $\sigma^2$ AND THE PHASE

The purpose of the preprocessing algorithm is (a) to combine the positive and negative pairs of phase alternated CPMG sequences, (b) to estimate the arbitrary phase difference between the received NMR signal and the phase reference of the coherent detector, thus reducing the two channel data to a single channel, (c) to stack the data to improve the signal to noise ratio, (d) to obtain an a priori estimate of the variance of the random noise in the stacked data.

Let us label the CPMG sequences by the index $k=0,1,2\ldots K$. When the tool is moving, each k corresponds to a different depth of the sonde. The CPMG sequence starts with the $90°_{+x}$ RF-pulse when $k=0,2,4,6\ldots$ and with the $90°_{-x}$ RF-pulse when $k=1,3,5,\ldots$. The j th echo of the k th CPMG sequence produces the noisy signals $r_{kj}$ and $x_{kj}$ at the output of the inphase and quadrature detectors. The preprocessing is as follows:

PREPROCESSING, STEP 1

The phase is constant over long sections of the log; it changes when the tuning capacitors or the oscillator frequency is altered. Suppose the tuning of the instrument is unchanged during the CPMG sequences $k=0,1\ldots K$. The phase is estimated according to [14]:

$$\hat{\theta}_k = \frac{1}{2} ATAN2(2<R, X>, <R, R> - <X, X>) \quad (A.1)$$

$$<R, X> = \sum_{l=1,3,5,\ldots}^{L_k} \sum_{j=1}^{N} (r_{l-1,j} - r_{l,j})(x_{l-1,j} - x_{l,j}) \quad (A.2)$$

$$L_k = \begin{cases} int[(k+1)/2], \text{ for real-time processing} \\ int[(K+1)/2], \text{ for post-processing} \end{cases} \quad (A.3)$$

where $int[(k+1)/2]$ is the integer part of $(k+1)/2$. The definitions for the terms (R,R) and (X,X) are similar to (A.2). If the data is being processed after the log has been recorded, first the phase is estimated using an entire section of the log in which the capacitors and the oscillator frequency is kept fixed. In this case, $\hat{\theta}_k$ is independent of k.

PREPROCESSING, STEP 2

The phase estimated in Step 1 is uncertain by an integer multiple of 180°. The correct sign is estimated as follows:

$$q_k = sgn\left(\sum_{l=1,3,5,\ldots}^{L_k} \sum_{j=1}^{N} \{(r_{l-1,j} - r_{l,j})\cos\hat{\theta}_k + (x_{l-1,j})\sin\hat{\theta}_k\}\right) \quad (A.4)$$

$$c_k = q_k \cos\hat{\theta} \quad (A.5)$$

$$s_k = q_k \cos\hat{\theta} \quad (A.6)$$

The factor $q_k$ takes the values $\pm 1$. In post-processing, $q_k$, $c_k$, and $s_k$ are independent of k.

PREPROCESSING, STEP 3

The signal is stacked as follows:

$$y_{k,j} = CAL * \left[ c_k \sum_{l=k-2S+1}^{k} (-1)^l r_{l,j} + s_k \sum_{l=k-2S+1}^{k} (-1)^l x_{l,j} \right] \quad (A.7)$$

where 2S is the depth of the stack, which must be an even number for cancellation of the baseline. The constant CAL is such that $y_{k,j}$ is in porosity units.

Each vector $y_k = [y_{k,1}; y_{k,2}; \ldots y_{k,N}]^T$ is a complete data set that can be processed. Once $k > 2S-1$, each time a new CPMG is acquired, there is a new set of data to be processed; there is no need to wait for a new pair of CPMG sequences to process the data.

PREPROCESSING, STEP 4

The noise in the entries of the vector $y_k$ are independently and identically distributed. (They are independently distributed because they depend on white noise collected on disjoint time intervals.) The variance of the noise can be estimated as follows:

$$\hat{\sigma}_k^2 = \frac{1}{(int[N/3] - 1)} \sum_{j=1}^{int[N/3]} w_{k,j}^2 \quad (A.8)$$

$$w_{k,j} = \frac{y_{k,3j-2} - 2y_{k,3j-1} + y_{k,3j}}{\sqrt{6}} \quad (A.9)$$

because the noise in $w_j$ are independently and identically distributed, also with the variance $\sigma^2$. Furthermore, $$E[w_{k,j}] \approx \phi \left(\frac{2t_{cp}}{T_2}\right)^2 e^{-2jt_{cp}/T_2} << \phi \quad (A.10)$$

for a single-exponential decay. The $\phi$ stands for porosity. Under typical borehole logging conditions, the terms $w_{k,j}$ contain all noise and negligible amount of signal. The formula (A.8) is satisfactory when $$\phi \left(\frac{2t_{cp}}{T_2}\right)^2 < \sigma \quad (A.11)$$

$N \geq 30$

The estimate $\hat{\sigma}_k^2$ of the variance should be fairly constant through out the log. Its significant deviations from a constant value are diagnostic of hardware or software failures. Also, $\hat{\sigma}_k^2$ should be approximately equal to the mean square fit error obtained after the inversion, which is provides a verification of the inversion.

DETERMINATION OF THE SINGULAR VALUE DECOMPOSITION, STEP 120

The singular value decomposition is obtained by finite number of operations as described below. To obtain the singular value decomposition of the operator K, first form the real, symmetric, positive semi-definite matrix G whose entries are the inner products of the kernels:

$$G_{ij} = <g_i, g_j> \quad (B.1)$$

The kernels are equal to $$g_j = \begin{cases} 1 - e^{-T_{rj}/T_1} & \text{for inversion-recovery} \\ e^{-2jt_{cp}/T_2} & \text{for } T_2 \text{ decay measurement} \\ (1 - e^{-T_r/\xi T_2}) e^{-2jt_{cp}/T_2} & \text{for the preferred protocol} \end{cases} \quad (B.2)$$

The entries of the matrix G are computed in terms of the exponential integral function $E_l$. Reference: M. Abramowitz and I. A. Stegun, Ed., "Handbook of Mathematical Functions," Dover, 1972.

$$E_1(x) = \int_x^\infty \frac{e^{-z}}{z} dz \quad (B.3)$$

-continued

For inversion recovery, $$G_{ij} = \log(T_b/T_a) + E_1\left(\frac{T_{ri} + T_{rj}}{T_b}\right) - E_1\left(\frac{T_{ri} + T_{rj}}{T_a}\right) + \quad \text{(B.4)}$$

$$E_1(T_{ri}/T_a) - E_1(T_{ri}/T_b) + E_1(T_{rj}/T_a) - E_1(T_{rj}/T_b)$$

For a CPMG measurement ensuing a full polarization, $$G_{ij} = E_1\left(\frac{2(i+j)t_{cp}}{T_b}\right) - E_1\left(\frac{2(i+j)t_{cp}}{T_a}\right) \quad \text{(B.5)}$$

For the preferred protocol (2), $$G_{ij} = E_1\left(\frac{2(i+j)t_{cp}}{T_b}\right) - E_1\left(\frac{2(i+j)t_{cp}}{T_a}\right) + \quad \text{(B.6)}$$

$$E_1\left(\frac{2T_r + 2(i+j)\xi t_{cp}}{\xi T_b}\right) - E_1\left(\frac{2T_r + 2(i+j)\xi t_{cp}}{\xi T_a}\right) -$$

$$2E_1\left(\frac{T_r + 2(i+j)\xi t_{cp}}{\xi T_b}\right) + 2E_1\left(\frac{T_r + 2(i+j)\xi t_{cp}}{\xi T_a}\right)$$

The left singular vectors $u_j$ are the eigen vectors of the matrix G and the singular values $s_j$ are the square root of the eigen values of G:

$$Gu_j = s_j^2 u_j \quad \text{(B.7)}$$

The eigen values and the eigen vectors can be computed by standard algorithms (see. E. Anderson, *Lapack Users' Guide, Society of Industrial and Applied Mathematics Philadelphia*, 1992). However, this calculation can be done more efficiently making use of the fact that the matrix G is a Hankel matrix in the cases (B.5) and (B.6). When the order of the columns of a Hankel matrix is reversed, it becomes a Toeplitz matrix. Therefore, multiplication of a vector by G takes on the order of N $\log_2$ N operations. The largest few eigen vectors and eigen values of G are efficiently evaluated by the power iteration (G. H. Golub and C. F. VanLoan, "Matrix Computations," 1st Ed., Sect. 7.3, John Hopkins University Press, Baltimore, 1983).

The right singular functions $v_j$ are linear combinations of the measurement kernels:

$$v_j = \frac{1}{s_j} \sum_{i=1}^{N} u_{ij} g_i \quad \text{(B.8)}$$

where $u_{ij}$ is the i th entry in the j th singular vector.

The inventors have found that NMR can be used to estimate the unbound fluid volume (UFV). Specifically, using NMR well logging techniques, bound fluid volume (BFV) is measured, and subtracted from total porosity $\phi$ to estimate unbound fluid volume (UFV). The estimation of UFV indicates the amount of producible fluid in a formation being logged.

Bound and unbound fluid volumes are defined as:

$$BFV = \int_0^{T_c} a(T_1) dT_1 \quad \text{(c1)}$$

$$UFV = \int_{T_c}^{\infty} a(T_1) dT_1 \quad \text{(c2)}$$

$$BFV + UFV = \Phi \quad \text{(c3)}$$

where $\Phi$ is porosity, the total volume fraction of fluids in the rock and $T_1$ is the spin-lattice relaxation time. The cutoff relaxation time $T_c$ distinguishing BFV from UFV is empirically determined to be 50 ms for water saturated sandstones. The UFV computed from (c2) has been shown to correlate well with the volume of water that can be centrifuged out of the sample at a fixed pressure gradient, C. Straley, C. E. Morriss, W. E. Kenyon, and J. J. Howard, "NMR in Partially Saturated Rocks: Laboratory Insights on Free Fluid Index and Comparison with Borehole Logs," presented at the annual SPWLA meeting, Midland, Tex. 1991, The approach used in C. Straley et al., "NMR in Partially Saturated Rocks; Laboratory Insights on Free Fluid Index and Comparison with Borehole Logs," to evaluate UFV involves finding the function $a(T_1)$, which is a time consuming process hence unsuitable for logging at moderate speeds.

Since BFV is associated with rapidly relaxing components, less than the cutoff time of 50 ms, for example, BFV can be measured faster than UFV. Determining UFV requires measurement of slowly relaxing components from 50 ms up to 2 seconds. If the total porosity $\Phi$ is known from some other measurement, UFV can be obtained by subtracting BFV from the total porosity.

Figure 4:
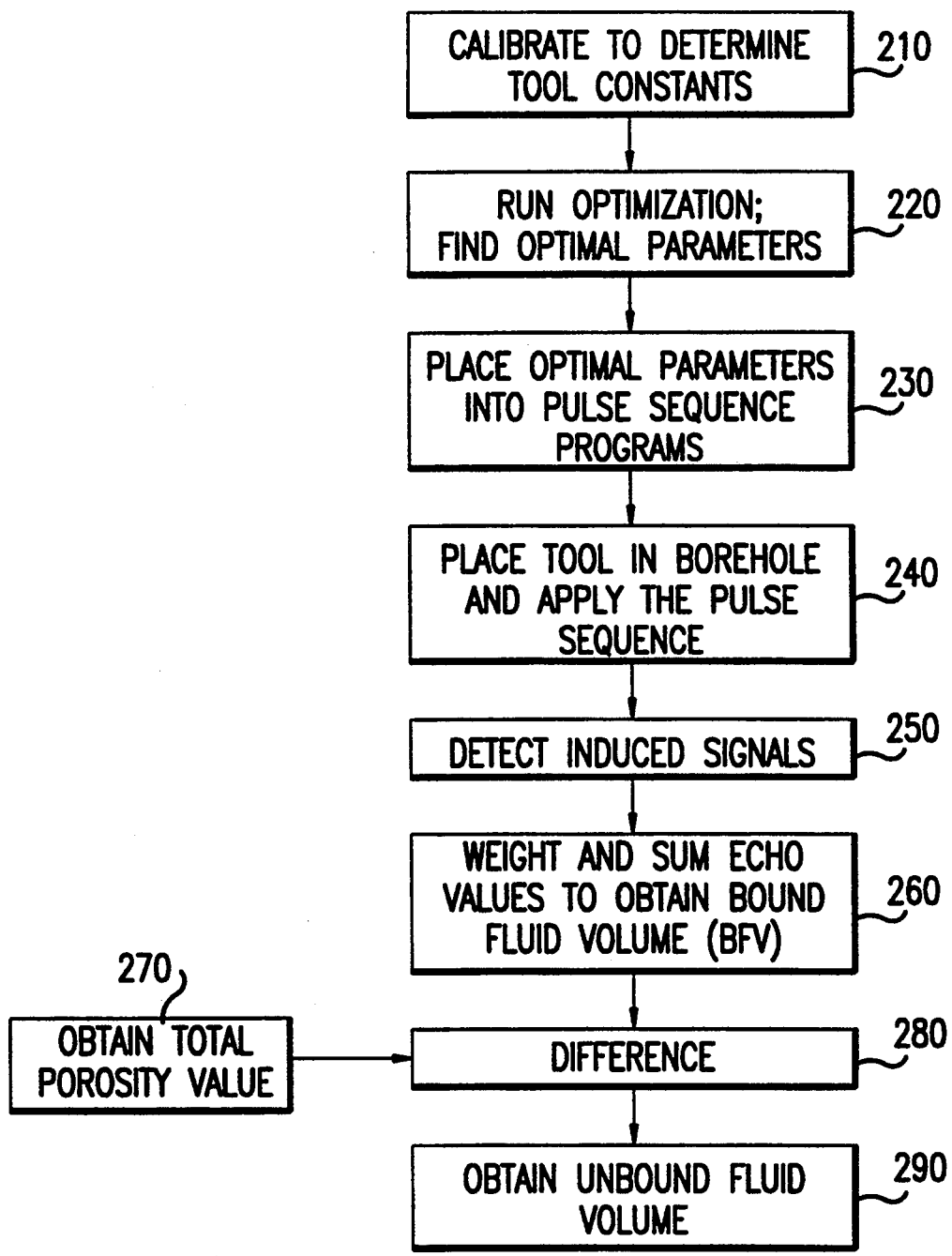
FIG. 4 is a flow chart illustrating steps for determining Bound Fluid volume (BFV) as described in U.S. patent application Ser. No. 7/800,339.

FIG. 4 is a flow chart illustrating steps for determining Bound Fluid Volume (BFV) of a formation. At 210, a calibration is performed to determine tool constants. At 220, desired parameters are entered, and an optimization is performed to find the optimal parameters. Specifically, the accuracy of the BFV estimate is optimized: the most accurate measurement is determined for a given amount of time. See the discussion below concerning Equation (c10). At 230, the optimal parameters are used in pulse sequence programs. Steps 210 and 230 are described in U.S. Pat. No. 5,023,551 to Kleinberg et al. At 240, a PNMT logging tool, for example, is placed in the borehole. The PNMT produces a static magnetic field in the volume of formation and then produces oscillating magnetic fields according to a pulse sequence $$T_r - 90°35x - (t_{cp} - 180°y - t_{cp} - \text{echo}_j)$$

where j=1, 2, . . . J, and J is the number of echoes collected in a single Carr-Purcell-Meiboom-Gill (CPMG) sequence to induce signals in the volume which are measurably by the PNMT in the borehole; where $T_r$ is recovery time before a CPMG sequence, and where $t_{cp}$ is the Carr-Purcell spacing. The pulse sequence is obtained by the optimization procedure of step 220. This pulse sequence is also discussed below concerning equations (c4) and (c5). At 250, the PNMT tool then detects resulting signals which have been induced in the formation around the borehole. At 260, echo values are weighted and summed as discussed below concerning equation (c1) and FIG. 5, for example. At 270, total porosity is obtained. Total porosity can be obtained with the PNMT itself. However, logging for porosity with this tool is relatively time consuming. In a preferred technique, total porosity is obtained using a Litho Density Tool (LDT, mark of Schlumberger), Compensated Neutron Log (CNL, mark of Schlumberger) or Sonic tool. Examples of tools for obtaining porosity are described in U.S. Pat. Nos. 3,453,433 to Alger et al. and 4,686,364 to Herron; 3,567,936 to Tittman and 3,567,935 to Negal; and 3,590,228 to Burke and 3,896,668 to Anderson et al. U.S. Pat. No. 3,638,484 to Tixier and 4,310,887 to Suau describe deriving porosity data using density, neutron and sonic tools. At 280, the difference between the total porosity $\Phi$ obtained in step 270 and the bound fluid volume (BFV) obtained at step 260 yields unbound fluid volume UFV at 290. UFV indicates the amount of producible fluid that is contained in the formation around the borehole being logged.

According to this invention, phase-alternated Carr-Purrcell-Meiboom-Gill (CPMG) sequences are used, which are separated by a fixed, relatively short recovery time ($T_r$=20 ms);

$$T_r \text{CPMG}^{(+)} T_r \text{CPMG}^{(-)} T_r \text{CPMG}^{(+)} T_r \text{CMG}^{(-)} \tag{c4}$$

where each CPMG sequence yields a short train of spin-echoes:

$$\text{CPMG}^{(\pm)} = 90°_{\pm x}[t_{cp} 180°_y t_{cp} \pm \text{echo}_j]\text{repeat for } j=1, 2, \ldots, J \tag{c3}$$

and $t_{cp}$ is half of the echo spacing (about 0.2 ms). $90°_{\pm x}$ denotes an RF-pulse that causes the spins to rotate by a 90° angle about the axis $\pm x$. Similarly $180_y$ denotes an RF-pulse that causes a rotation by 180° about the axis y. The z-axis is parallel to the static field, the x-axis is in the direction of the circularly polarized component of the RF-field ($B_1$) that rotates in the same direction as the spins precess. The reference frame (x,y,z) rotates around the z axis with the angular frequency of the RF-field.

An estimate of the BFV is obtained by a weighted sum of the echoes:

$$\overline{BFV} = \sum_{j=1}^{J} w_j \text{echo}_j \tag{c6}$$

The overbar denotes the estimate of the BFV as opposed to the quantity defined in (c1).

Figure 5:
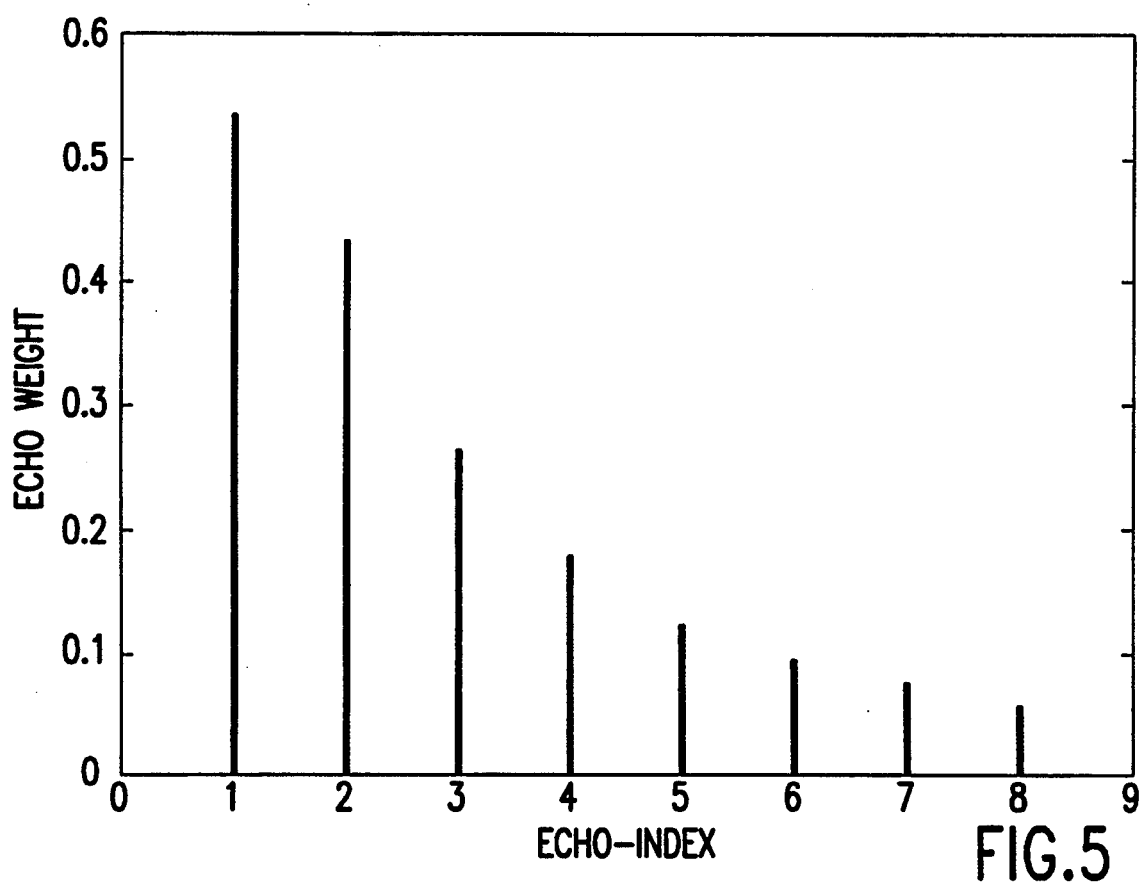
FIG. 5 is a chart illustrating an example of weights applied to pulse echoes to obtain BFV as described in relation to FIG. 4.

FIG. 5 is a chart illustrating an example of values of weights applied to echoes to obtain $\overline{BFV}$. Echo-Weight is plotted as a function of Echo-Index. These Echo-Weights were applied to echoes to obtain $\overline{BFV}$ for Carr-Purcell spacing $t_{cp}$=0.2 ms and the ratio of spin-lattice relaxation time ($T_1$) to spin-spin relaxation time ($T_2$) $T_1/T_2$ is 1.5. The variance of the estimate of after stacking for T seconds is $$\text{Var}[\overline{BFV}] = \frac{T_r + 2Jt_{cp}}{T} \sigma^2 w^2 \tag{c7}$$

$$w^2 = w_1^2 + w_2^2 + \ldots + w_J^2$$

where each echo has independently and identically distributed, zero-mean, additive Gaussian noise of standard deviation $\sigma$, which is about porosity units for the PNMT. $T_r$ is the length of the recovery-time in between the CPMG sequences. w is the norm of the vector $w=(w_1, w_2, \ldots, w_J)$. The estimator of BFV is a linear functional that acts on the relaxation-time distribution:

$$\overline{BFV} = \int_0^\infty f(T_1) a(T_1) dT_1 \tag{c8}$$

where $f(T_1)$ is a weighting function (not to be confused with the echo-weights $w_j$):

$$f(T_1) = [1 - e^{-T_r/T_1}] \sum_{j=1}^{J} w_j \exp\left(\frac{-2jt_{cp}(T_1/T_2)}{T_1}\right) \tag{c9}$$

The above expression is simplified by the fact that the ratio $T_1/T_2$ is approximately constant. It is unity for bulk water samples and about 1.5 for water saturated sandstones.

Also taken into account in the computation, but not shown in (c9), is the fact that in a CPMG pulse-echo sequence the first spin-echo is about 61% of what would be expected from the extrapolation of the other echoes. This is a consequence of spin-dynamics in inhomogeneous fields and it has been verified by numerical solutions of Bloch's equation. The factor 61% was experimentally determined.

The adjustable parameters of the measurement, namely, ($w_1, w_2, \ldots, w_J$), $T_r$, J are determined by two competing requirements. First according to (c1) and (c8), $$f(T_1) \approx \begin{cases} 1, \text{ if } T_1 < T_c \\ 0, \text{ if } T_1 > T_c \end{cases} \tag{c10}$$

must be satisfied. On the other hand, according to (C7), w must be kept small in order to keep the statistical error small. Equation (c10) has been solved for w in the least square sense subject to the constraint w<constant. The parameters $T_r$ and J have been determined by trial and error to minimize the least square error in (c10). The result of the optimization yielded J=8, $T_r$=20 ms and a set of weights $w_j$ that decreases with increasing j which are shown in FIG. 4.

Figure 6:
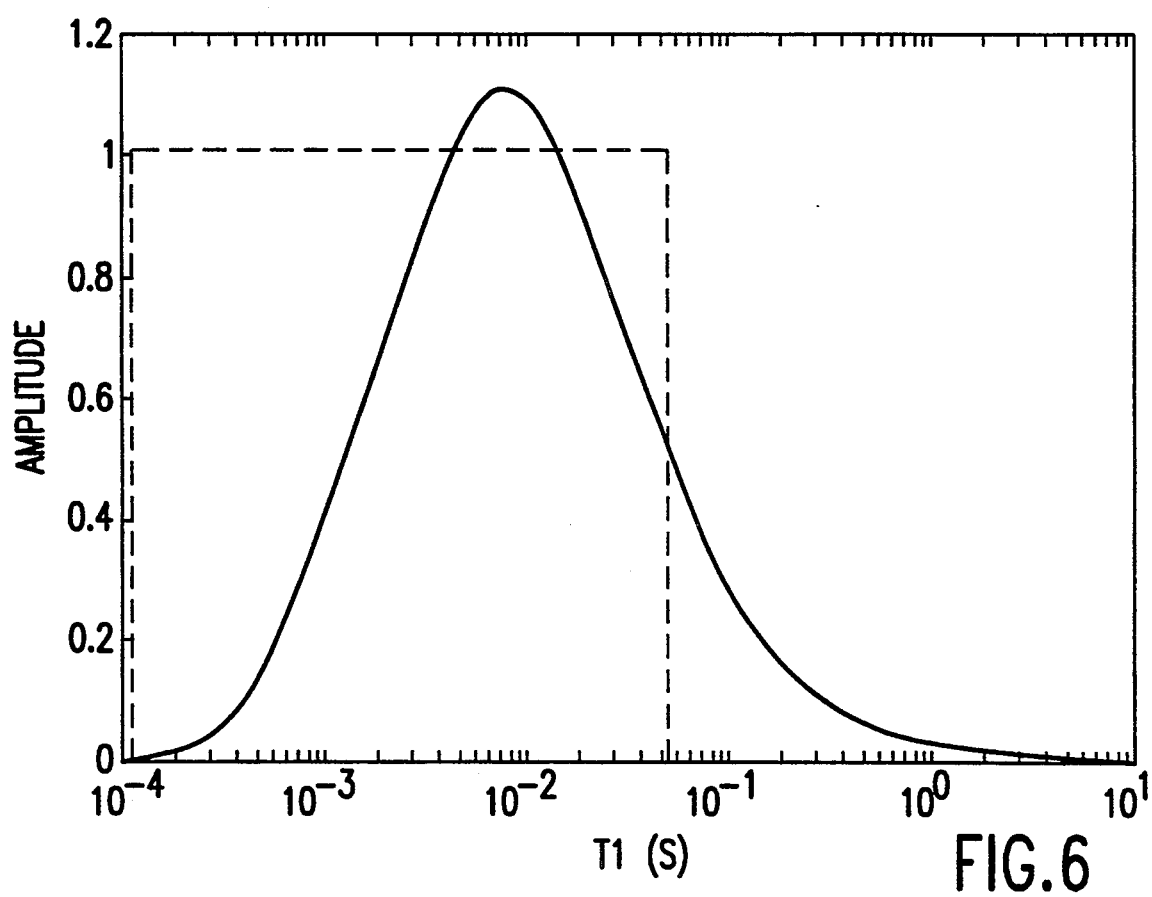
FIG. 6 is a chart illustrating an example of actual and ideal weighting parameters.

FIG. 6 is a chart illustrating an example of actual and ideal weighting functions. Amplitude is plotted as a function of spin lattice relaxation time $T_1$ in seconds. The solid line shows an actual weighting function $f(T_1)$ and the dashed line shows an ideal weighting function. In this case, $t_{cp}$=0.2 ms, recovery time $T_r$=20 ms, J=8, $T_1/T_2$=1.5, and the weights are as shown in FIG. 5. As intended, the weighting function has a long-time cut-off because slowly relaxing components can not recover in the short recovery time. There is also a short-time cut-off (see FIG. 6) because the components that significantly decay before the first echo are not observed.

A short-time cut-off is needed so that the tool is insensitive to hydrogen in the rock matrix. The short-time cut-off around 1 ms shown in FIG. 6 is probably higher than needed: same clay-bound water may be missed. However, if the total porosity measurements has the same short-time cut-off, no error will be introduced in the estimation of UFV.

For $t_{cp}$=0.2 ms, $T_r$=20 ms, J=8, $\sigma$=10 p.u., and signal accumulation time T=1 s, the standard deviation of BFV is 1.2 p.u. For $t_{cp}$=0.35 ms, the standard deviation is 1.4 p.u.

I claim:

1. A method for measuring an indication of an attribute of a volume of earth formation with a borehole tool having means for producing static magnetic fields in a volume of a formation, means for producing oscillating magnetic fields in a volume of a formation, and means for measuring an induced magnetic signal, the method comprising:
   a) producing a static magnetic field in the volume of formation;
   b) producing oscillating magnetic fields according to a pulse sequence $$T_r - 90°\pm x - (t_{cp} - 180°y - t_{cp} - \text{echo}_j)$$

where $j = 1, 2 \ldots N$, and N is the number of echoes collected in a single Carr-Purcell-Meiboom-Gill (CPMG) sequence in order to induce signals in the volume which are measurable by the tool in the borehole;
      where $T_r$ is recovery time before a CPMG sequence, and
      where $t_{cp}$ is the Carr-Purcell spacing;
   c) using a linear operator to map a relaxation-time distribution to resulting spin echoes,
   d) producing a singular value decomposition (SVD) of the linear operator according to the pulse sequence;
   e) measuring with the tool the induced signals; and
   f) determining from the measured signals an indication of unbound fluid volume (UFV) of the volume of earth formation in light of the SVD.

2. A method according to claim 1, wherein the induced signals represent field data, the steps comprising:
   g) determining orthonormal right and left-singular vectors of the SVD; and
   h) compressing the field data using the orthonormal left-singular vectors.

3. A method according to claim 2, comprising:
   using the compressed field data and the SVD in solving a constrained linear least squares.

4. A method according to claim 3, comprising:
   deriving an estimation of a distribution f of relaxation-times from the compressed data.

5. A method according to claim 4, comprising:
   selecting a regularization parameter to minimize $\|f_\alpha - f\|$ where $f_\alpha$ is the nonnegative distribution that minimizes a fit error $\chi$ with regard to f plus a regularization term with a prefactor $\alpha$.

6. A method according to claim 5, comprising:
   iterating the selection of the regularization parameter by repeatedly solving the constrained least squares.

7. The method of claim 6, the steps comprising a determining the regularization parameter $\alpha$ according to an S-curve approach such that $\alpha$ is the smallest value satisfying $$\frac{d(\log \chi)}{d(\log \alpha)} = tol$$

where $\chi$ is the fit error $\|y - Kf\|$, y is the data vector and K is the linear operator that maps the relaxation-time distribution to the spin-echoes, and tol is prefixed constant between 0 and 1.

8. The method of claim 7, the steps comprising: using the compressed data for determining the data vector y, deriving, $\sigma^2$ an a priori estimate of variance of the data vector y, for use in determining the SVD.

9. The method of claim 8, the steps comprising:
   determining the regularization parameter $\alpha$ according to a Butler-Reeds-Dawson (BRD) approach using the estimate of variance $\sigma^2$.

10. The method of claim 9, the steps comprising:
    selecting a larger regularization parameter $\alpha$ of two $\alpha$'s, one determined according to the S-curve approach and one determined according to the BRD approach.

11. The method of claim 10, the steps comprising:
    deriving an estimated distribution of spin-spin relaxation time from the compressed data.

12. The method of claim 11, the steps comprising:
    using $\sigma^2$ in determining which terms of the SVD are relevant.

13. The method of claim 12, the steps comprising:
    using a pulsed nuclear magnetic tool (PNMT) to produce magnetic fields in the formation.

14. The method of claim 13, the steps comprising:
    storing the SVD in a memory connected to the PNMT.

15. A method according to claim 14, comprising:
    determining bound fluid volume (BFV), porosity, $\phi$ and mean relaxation using the spin-spin relaxation time.

16. A method according to claim 15, wherein UFV, BFV, $\phi$ and mean relaxation are determined using a borehole tool having a means for producing static magnetic fields and no other borehole tool.

17. The method of claim 6, the steps comprising:
    determining the regularization parameter according to a Butler-Reeds-Dawson (BRD) appoach using an estimate of variance $\sigma^2$ of the compressed data.

18. The method of claim 17, the steps comprising:
    deriving an estimated distribution of spin-spin relaxation time from the compressed data.

19. The method of claim 18, the steps comprising:
    using $\sigma^2$ in determining which terms of the SVD are relevant.

20. The method of claim 19, the steps comprising:
    using a pulsed nuclear magnetic tool (PMT) to produce magnetic fields in the formation.

21. The method of claim 20, the steps comprising:
    storing the SVD in a memory connected to the PNMT.

* * * * *